United States Patent [19]

Yanaka et al.

[11] Patent Number: 5,312,977
[45] Date of Patent: May 17, 1994

[54] METHOD FOR PURIFYING L-PHENYLALANINE

[75] Inventors: Makoto Yanaka; Tooru Miyahara; Daisuke Ura; Nobuhiro Fukuhara, all of Ohmuta, Japan

[73] Assignee: Mitsui Toatsu Chemicals, Incorporated, Tokyo, Japan

[21] Appl. No.: 19,116

[22] Filed: Feb. 17, 1993

[30] Foreign Application Priority Data

Feb. 17, 1992 [JP] Japan ................................. 4-029205

[51] Int. Cl.$^5$ .......................................... C07C 229/28
[52] U.S. Cl. .................................................. 562/443
[58] Field of Search ........................................ 562/443

[56] References Cited

U.S. PATENT DOCUMENTS 4,173,469  3/1988  Evans et al. .

FOREIGN PATENT DOCUMENTS 0140713  5/1985  European Pat. Off. .
0165757  12/1985  European Pat. Off. .

OTHER PUBLICATIONS

Database WPIL, Week 8410, AN 84–058415 & JP-A-59 014 796 Jan. 25, 1984.
Patent Abstracts of Japan, vol. 11, No. 96 (C–412) (2543) Mar. 26, 1987.
Patent Abstracts of Japan, vol. 9, No. 211 (C–300)(1934) Aug. 29, 1985.
Database WPIL, Week 8641, AN 86–267881 & JP-A-61 194 056 Feb. 21, 1985.

*Primary Examiner*—Jose G. Dees
*Assistant Examiner*—Joseph M. Conrad, III
*Attorney, Agent, or Firm*—Millen, White, Zelano & Branigan

[57] ABSTRACT

L-Phenylalanine is isolated in pure form from an aqueous solution thereof containing cinnamic acid by subjecting the aqueous solution to toluene extraction to extract cinnamic acid therefrom; separating the toluene phase; and then concentrating the aqueous phase, until crystals of L-phenylalanine form therein, while concurrently separating the crystalline L-phenylalanine from the liquid aqueous phase.

20 Claims, 1 Drawing Sheet

METHOD FOR PURIFYING L-PHENYLALANINE

BACKGROUND OF THE INVENTION (i) Field of the Invention

The present invention relates to an improved method for purifying L-phenylalanine which is suitable for the purification of L-phenylalanine produced by a reaction using cinnamic acid as a starting material and phenylalanine ammonia lyase in the presence of ammonia.

(ii) Description of the Prior Art

L-phenylalanine is an essential amino acid which is used as a medicine such as an amino acid transfusion, and is an important component as a constitutional amino acid of α-L-aspartyl-L-phenylalanine methyl ester which is a peptide sweetener.

Manufacturing methods of L-phenylalanine can be classified into a chemical synthesis method, a fermentation method and residual an enzyme method. An example of the enzyme method comprises using cinnamic acid as a starting material and phenylalanine ammonia lyase in the presence of ammonia. This reaction is reversible, and cinnamic acid which is the starting material remains in the reaction solution. Therefore, the remaining cinnamic acid must be removed in a purification step to efficiently collect the L-phenylalanine.

As purification methods for L-phenylalanine, there have been employed a method using an ion exchange resin adsorbent (Japanese Patent Application Laid-open No. 194056/1986), a method using concentration/crystallization (Japanese Patent Application Laid-open No. 133893/1985) and a method using a lower alcohol (U.S. Pat. No. 4731469).

The above-mentioned purification methods of L-phenylalanine have the following problems in the case they are utilized on an industrial scale.

In the ion exchange resin adsorption method, the L-phenylalanine is separated from the cinnamic acid by chromatography, as described in Japanese Patent Application Laid-open No. 194056/1986. In this method, however, volumetric efficiency is poor and what is worse, enormous energy is consumed. For these reasons, the method is inconvenient for mass production.

In the above-mentioned method using concentration/crystallization, the pH of an aqueous L-phenylalanine solution containing cinnamic acid is adjusted to 6–9, and after concentration, cooling and crystallization are carried out, as described in Japanese Patent Application Laid-open No. 133893/1985. However, it is difficult to completely separate the cinnamic acid by this method. This Japanese Patent Application Laid-open No. 133893/1985 also describes another method which comprises adjusting the pH of an aqueous L-phenylalanine solution containing cinnamic acid to a level of strong acidity, removing precipitated cinnamic acid, and then purifying L-phenylalanine. However, in order to remove the cinnamic acid, a separating operation such as filtration of the strongly acidic solution must be carried out. Therefore, the operation is troublesome and its volumetric efficiency is low. Since L-phenylalanine high soluble in the strongly acidic state, the solution must be neutralized to an isoelectric point or its vicinity of L-phenylalanine, after the removal of cinnamic acid. Thus, a large amount of salts is inconveniently formed, even though the cinnamic acid can be removed.

In the method using a lower alcohol, a lower alcohol is added to a concentrated solution of L-phenylalanine, so that the cinnamic acid is dissolved in the lower alcohol and thus it is removed, as described in U.S. Pat. No. 4731469. In this method, however, a large amount of the lower alcohol is necessary, for example, about five times by weight of the L-phenylalanine. Accordingly, the yield of L-phenylalanine lowers, the volumetric efficiency deteriorates, and large facilities for the recovery of the solvent are required, even though cinnamic acid can be removed. In addition, in manufacturing L-phenylalanine, the recovery of unreacted cinnamic acid is a serious problem, but a crystallization filtrate from which L-phenylalanine has been separated contains a large amount of impurities, so that the recovered cinnamic acid inconveniently has a low purity.

Furthermore, the solubility of L-phenylalanine in water is low, and so there remains a problem that when the crystals of L-phenylalanine are deposited from an aqueous L-phenylalanine solution, the volumetric efficiency is very poor.

SUMMARY OF THE INVENTION

An object of the present invention is to provide a method which comprises effectively separating L-phenylalanine from residual cinnamic acid employed as a starting material in the preparation of L-phenylalanine to obtain high-quality L-phenylalanine in a high yield advantageously on an industrial scale.

The present inventors have intensively made investigation to solve the above-mentioned problems, and they have found that the crystals of L-phenylalanine can be effectively separated from an aqueous L-phenylalanine solution containing cinnamic acid by concentrating the aqueous L-phenylalanine solution, separating a part or all of the solution after recipitation of L-phenylalanine crystals begins, carrying out solid-liquid separation to remove the precipitation L-phenylalanine therefrom, returning the liquid phase only to the concentrated solution, and continuously or intermittently continuing the concentration of the solution. Furthermore, because when a large amount of cinnamic acid is present in the concentrated solution, the yield of cinnamic acid-free L-phenylalanine decreases, of portion of the cinnamic acid in the starting solution is first extracted with toluene.

The method of the present invention is particularly useful for isolating pure L-phenylalanine from a reaction solution obtained by a reaction using cinnamic acid as a starting material and phenylalanine ammonia lyase in the presence of ammonia.

According to the present invention, L-phenylalanine can be effectively separated from cinnamic acid, whereby high-quality L-phenylalanine can be purified in a high yield and advantageously on an industrial scale.

DETAILED DESCRIPTION OF THE PREFERRED EMBODIMENTS

Figure 1:
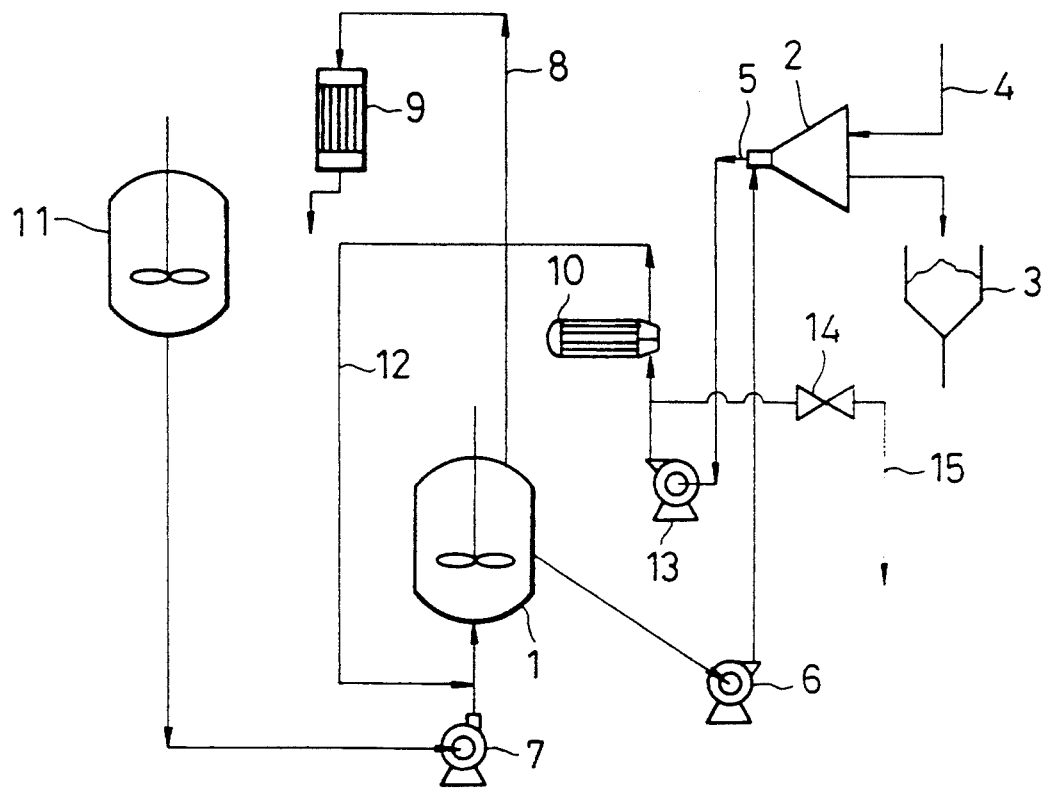
FIG. 1 shows an example of the system for the step (b) of the present invention.

A method of the present invention for purifying L-phenylalanine comprises the steps of (a) subjecting an aqueous solution containing mainly cinnamic acid and L-phenylalanine to toluene extraction to extract cinnamic acid therefrom followed by separating the extracting toluene solution from the extracted aqueous solution; (b) concentrating as an aqueous liquid phase the separated extracted aqueous solution until a solid phase comprising crystals of L-phenylalanine forms therein; and (c), concurrently with step (b), separating by solid/liquid separation the solid phase comprising crystals of L-phenylalanine from the aqueous liquid phase.

The concentration of L-phenylalanine in the starting aqueous solution employed in step (a) is preferably concentrated to 6% by weight or less, more preferably 4% to 6% by weight. The concentration of cinnamic acid of the aqueous solution in the step (a) is preferably less than 0.6% by weight and more than 0.01% by weight.

The aqueous solution in starting step (a) is preferably heated to a temperature necessary for dissolution of The extraction using toluene in the step (a) may be L-phenylalanine, preferably in the range from 60°–80° C.

The toluene in step (a) may be carried out at a pH less than 5, preferably less than 4.5. If the pH is 5 or more than, the extracting efficiency is extremely reduced. For example, when 15 parts by weight of toluene and 100 parts by weight of an aqueous solution mainly containing L-phenylalanine and cinnamic acid are mixed and agitated at 70° C. for 15 minutes, and the resulting mixture is then allowed to stand, the extraction efficiency is only about 10% at pH 5.5, but can reach about 70% at pH 4.0.

The pH regulation of the aqueous solution can be carried out by adding an acid such as sulfuric acid, hydrochloric acid and phosphoric acid.

Toluene is added to the aqueous solution for extraction in an amount of less than 50 parts by weight, preferably 8–15 parts by weight, per 100 parts by weight of the aqueous solution No particular limitation is placed on the operating conditions for the extraction, which can be determined so that cinnamic acid can be effectively extracted into the toluene phase. example, the aqueous solution and toluene are mixed agitated at 70° C. for 15 minutes and, if necessary, the extraction procedure can be repeated.

The aqueous phase thus obtained from the starting aqueous solution mainly containing L-phenylalanine and cinnamic acid and toluene is then recovered and concentrated in step (b). Introduction of the step (a) prior to step (b) can result complete in removal of the cinnamic acid from the final product or extremely reduce the cinnamic acid content thereof.

In Step (b), the separated aqueous phase obtained in step (a) is concentrated concurrently with removal therefrom of any residual toluene from the toluene phase employed in Step (a). Conducting step (a) prior to Step (b), results in removal of all or substantially all of the cinnamic acid from the final product. By conducting the concentration step of Step (b) on the separated aqueous phase obtained in step (a), cinnamic acid is not occluded in the solid materials precipitated in the concentration procedure.

The step (b) can be carried out, for example, by the process shown in FIG. 1.

The extract aqueous solution obtained as the aqueous phase containing L-phenylalanine and residual cinnamic acid obtained in the step (a) is accumulated in tank 11, in which the concentration of L-phenylalanine may be adjusted, if required (by means not shown) by dilution with or addition of water thereto. The aqueous solution phase is supplied through pump 7 from the tank 11 to concentrator 1. Since no particular limitation is placed on concentrator 1, any concentrator can be used. For example, a concentrator having a jacket or tubular heater, and preferably a draft tube to promote growth of crystals, can be used. Vapor in concentrator 1 flows to condenser 9 through the vapor line 8 connected to the upper part of concentrator 1. In the condenser 9, the vapor is condensed and removed from the system.

Regarding the influence of racemization on concentration, the aqueous solution is concentrated in concentrator 1 preferably at a temperature of 70° C. or below. However, if the temperature is too low, huge and excess equipment for providing the vacuum for concentrator 1 including a vacuum pump is required. Therefore, the temperature for the concentration is more preferably regulated between 50° and 70° C.

When the L-phenylalanine crystals have formed in concentrator 1, a slurry including the crystals is transferred up slurry pump 6 to a solid/liquid separator 2 such as a decanter.

The crystals separated from liquid in separator 2 are then collected in crystal receiver 3. The crystals may be washed in separator 2 by a washing agent supplied through washing line 4. A liquid fraction is removed from the separator through line 5 to pump 13 and divided into line to the heater 10 and two streams, one going through line to the heater 10 and a other through purge line 15. The liquid from the heater 10 is then returned to concentrator 1 through the feed back line 12.

The procedure using the system shown in FIG. 1 may be carried out continuously or intermittently.

In the continuous procedure, the aqueous solution is continuously supplied from tank 11 to concentrator 1 through pump 7, and a part of the liquid from separator 2 is purged through purge line 15 including purge valve 14. The other parts of the system are also operated continuously.

In the intermittent procedure, the aqueous solution is supplied from tank 11 to the concentrator, and, when the concentrator is filled with the aqueous solution, the supply of the aqueous solution thereto from tank 11 is stopped. The other parts of the system for the concentration and solid/liquid separation are operated in the same manner as in the above continuous procedure. When the L-phenylalanine concentration of the solution in concentrator 1 reaches 15% by weight, fresh aqueous solution is supplied from tank 11 to the concentrator 1 until the concentrator is again full.

When this purification method is used as a purification process in the manufacture of L-phenylalanine by the use of phenylalanine ammonia lyase, a more effective and industrially advantageous method for preparing L-phenylalanine is provided.

A method for preparing L-phenylalanine of the present invention comprises the steps of:

i. reacting cinnamic acid with an ammonia source in the presence of phenylalanine ammonia lyase to obtain a reaction solution;

ii. obtaining a clarified liquid phase from the reaction solution by liquid-solid separation;

iii. removing the ammonia source from the clarified liquid;

iv. extracting the clarified liquid obtained from step iii with toluene;

v. while an aqueous phase obtained by the above-mentioned toluene extraction is concentrated; and vi. collecting the solid phase obtained in the step v as L-phenylalanine crystals.

Steps i to iii can be accomplished by known procedures, and steps iv to vi correspond to the purification method of the present invention.

The method of the present invention can be used in conjunction with an enzyme reaction for preparing L-phenylalanine which uses cinnamic acid as a starting material and phenylalanine ammonia lyase in the presence of ammonia, for example, bacterial cells obtained by culturing, for example, an *Escherichia coli* transformant, strain MT10423 (FERM BP-1713), carrying a phenylalanine ammonia lyase gene, or cells of the transformant immobilized on carriers are dispersed in a suitable ammonium source such as an ammonia-ammonium carbonate buffer solution (ammonia concentration=13-17% by weight, pH=9-11), and in this case, the amount of the bacterial cells or the immobilized bacterial cells is from 0.5 to 2.0% by weight in terms of the dry cell. The reaction is then carried out adjusting the temperature in a reactor to 30°-40° C. As described in Japanese Patent Application Laid-open No. 247395/1986, the reaction can be achieved by the use of 10 moles/liter of ammonia, 0.05 to 0.5 equivalents of carbonate ions in the presence of 0.05 mole/liter or less of cinnamic acid.

The reaction solution is subjected to centrifugal separation, filtration or the like to remove the bacterial cells and solids derived therefrom, thereby obtaining a clarified liquid. Furthermore, this clarified liquid is then treated by an operation such as evaporation at a temperature of 40°-100° C., preferably 40°-70° C. to remove the ammonia source, thereby obtaining an aqueous L-phenylalanine solution.

The aqueous L-phenylalanine solution is adjusted to an acidic pH with a mineral acid, and toluene is then added to and brought into contact with the solution, whereby a portion of the residual cinnamic acid therein can be extracted. Alternatively, after the pH adjustment, an active carbon treatment may be carried out, and the active carbon and materials to which the active carbon adheres are removed by filtration or other means and cinnamic acid may be then extracted with toluene from the active carbon-free solution at a temperature of 60°-80° C. at a pH of less than 5, preferably a pH of 4.5 or lower.

Cinnamic acid extracted with the toluene can be easily isolated therefrom and then reused in the reaction. One such process comprises taking out a toluene phase containing cinnamic acid, followed by evaporating the toluene, and another process which comprises adding fresh water to the solution to adjust its pH to an alkaline level and to thereby permit reverse extraction into an aqueous phase.

The thus obtained aqueous L-phenylalanine solution from which a part of the cinnamic acid has been removed by the extraction is then concentrated. If the aqueous L-phenylalanine solution from which cinnamic acid has not been extracted with toluene, the following concentration operation is operable but it is preferred that the extraction is conducted previously.

The concentration of the present invention can be carried out as follows: As described above, the aqueous L-phenylalanine solution is concentrated under atmospheric pressure or reduced pressure to bring about crystallization because the concentration of L-phenylalanine is in excess of a saturated solubility in the aqueous solution part or all of the crystal containing solution is then removed and subject to solid/liquid separation, while maintaining the temperature of the concentrated solution. The thus-obtained liquid phase is returned to the concentrated solution again and the solid phase thus-obtained is taken out. This operation of the concentration can be conducted continuously or intermittently.

As described above, the temperature during the concentration is preferably 70° C. or less, more preferably between 50° C. and 70° C., in consideration of the influence of racemization and the like. At the time of the concentration, the concentration of L-phenylalanine is preferably in the range of 8 to 15% by weight. When the solid/liquid separation is made at the concentration of less than 8% by weight, a throughput is large, and thus a large apparatus is required inconveniently. Conversely, when it is carried out at the concentration of more than 15% by weight, the viscosity of the solution increases, which deteriorates workability. In addition, the content of impurities in the crystals increases inconveniently. For the solid/liquid separation, a filter, a centrifugal separator and the like can be applicable, but it is preferred to use a decanter type centrifugal settler. Furthermore, the obtained solid phase is preferably washed with a suitable amount of warm water.

By concurrently separating the solid phase, i.e., the crystals of L-phenylalanine, obtained by continuously or intermittently concentrating the solution starting by solid/liquid separation in this way, the entrainment of impurities such as cinnamic acid in the L-phenylalanine can be inhibited, and the purity of the solid phase is thus higher than in the case of a conventional batch system concentration. In addition, the viscosity of the concentrated solution is sufficiently low, and hence operations such as solution transfusion and the filtration are very easy. The continuous operation permits the use of a very small concentrator and the improvement of a volumetric efficiency.

The thus obtained crystals of L-phenylalanine can be dried in the form they are obtained.

Furthermore, a lower alcohol can be added, at a temperature of its boiling point or less, to the crystals of L-phenylalanine obtained by the concentration in accordance with the method of the present invention, whereby T% can be improved. Examples of the above-mentioned lower alcohol include isopropyl alcohol, n-propyl alcohol, methyl alcohol and ethyl alcohol. The amount of the lower alcohol to be added is preferably in the range of from 50 to 150% by weight based on the weight of L-phenylalanine. If the amount of the lower alcohol is less than 50% by weight, the concentration of the solid is too high and the operation of sludging is inconveniently difficult. Conversely, if it is more than 150% by weight, the yield of L-phenylalanine and volumetric efficiency deteriorate and it is apparent that such an amount is not practical.

From the thus obtained sludging mass, the crystals of L-phenylalanine can be collected by an operation such as filtration. The resultant filtrate can be returned to the purification process, after the removal of the lower alcohol by a means such as evaporation.

In the following examples and comparative examples, the quantitative analysis of cinnamic acid in L-phenylalanine crystals was carried out by quantitatively analyzing an aqueous solution formed by diluting 0.1 g of crystals with 100 g of water through a liquid chromatography using an ultraviolet absorbing spectrophotometer attached to a detector. Conditions for the analysis are as follows:

Column: Fine Pack TSL C18 (Nippon Bunnko Co., Ltd.).

Mobile phase: 50% aqueous methanol solution whose pH was adjusted to 2 with phosphoric acid.

Detection wavelength: 280 nm

The detection limit of cinnamic acid under these conditions was 0.2 ppm.

The quantitative analysis of L-phenylalanine was carried out by the following procedure:

A sample (0.3 g) was exactly weighed and 50 ml of glacial acetic acid was added to the sample. The mixture was warmed to dissolve the sample and cooled to obtain a sample solution. After addition of 10 drops of a p-Naphtholbenzein indicator solution, the sample solution was titrated by a 0.1N perchloric acid solution. The sample result was corrected by the result obtained in the control. One milliliter of the 0.1N perchloric acid solution corresponded to 16.519 mg of L-phenylalanine.

EXAMPLE 1

A transformed *E. coli* strain MT 10423 was cultured and cells were collected by centrifugation. This strain 10423 was deposited as Deposition No. FERM BP-1713 on Oct. 31, 1986 and converted to the Budapest Treaty Status on Feb. 8, 1988 at the Fermentation Research Institute of the Agency of Industrial Science and Technology, 1-3, Higashi 1-chome, Tsukuba-gun, Ibaraki-ken, 305, Japan. This strain carries a phenylalanine ammonia lyase gene.

The collected cells (wet weight: 19.2 g; dry weight: 4.0 g) were suspended in 750 g of an ammonia-ammonium carbonate buffer solution (ammonia concentration=13% by weight, pH 10.4). Afterward, 47.8 g of powdery cinnamic acid were gradually added thereto over 16 hours, while the pH of a reaction solution was maintained at 10.4 with ammonia, to obtain 800 g of reaction solution. In this reaction solution, the amount of produced L-phenylalanine was 48.0 g and that of the remaining cinnamic acid was 4.8 g.

The cells were removed from this reaction mixture by centrifugal separation, and the resultant supernatant liquid was then heated at 70° C. to remove ammonia and ammonium carbonate, whereby an aqueous L-phenylalanine solution was obtained.

The pH of the aqueous L-phenylalanine solution was adjusted to 4.0 with concentrated sulfuric acid, and 100 g of toluene were then added thereto. After stirring for 15 minutes, standing/separation was carried out. This operation of the cinnamic acid extraction was repeated 4 times in all, and at this time, the concentration of cinnamic acid in a toluene phase was 1.19%. An aqueous phase was concentrated at 70° C. under reduced pressure as follows: The original solution to be concentrated was fed to a concentrator at 80 g/hr so that the amount of the solution in the concentrator would be 160 g and the concentration of L-phenylalanine would be 10% by weight. A portion of the concentrated solution was continuously drawn and then subjected to solid/liquid separation. A part of the resulting liquid phase was purged at 4.0 g/hr from the system, and the remainder was returned to the concentrator. During this operation, the temperature in the whole apparatus was maintained at 70° C. In the thus obtained crystalline solid phase the L-phenylalanine content was 34.4 g, and the cinnamic acid was less than a detection limit. The purity of the L-phenylalanine crystals as the solid phase was 99.5%.

EXAMPLES 2 TO 4

In each example, the same procedure as Example 1 was repeated three times except that an original solution to be concentrated which was obtained by the same procedure as in Example 1 was fed to an aqueous solution of L-phenylalanine in a concentrator which remained finally after the operation of Example 1. The results are set forth in Table 1. The purity of the L-phenylalanine crystals was 99.0% or more.

EXAMPLE 5 same procedure as Example 1 was repeated except that the pH of an aqueous L-phenylalanine solution after the removal of ammonium carbonate was adjusted to 4.0 with concentrated sulfuric acid, and 100 g of toluene were then added thereto, and after stirring for 15 minutes, standing/separation was conducted. The following operation was then carried out using 800 g of the thus obtained original solution to be concentrated (48.0 g of L-phenylalanine and 1.4 g of cinnamic acid).

This original solution was concentrated at 70° C. under reduced pressure until the concentration of L-phenylalanine therein was 10% by weight. The concentrated solution was then filtered, while the concentration temperature was maintained, to separate the crystals of L-phenylalanine. Next, the thus obtained crystals were washed with warm water at 70° C. in about the same amount as the crystals. The filtrate and the wash liquid were subjected to the similar operations of the concentration and the filtration again, and this cycle was repeated 7 times in all. The amount of the obtained crystals (purity 98.5%) was 45.5 g (dry weight) and the cinnamic acid content thereof was detection limit.

EXAMPLE 6

60 g of 80% isopropyl alcohol were added to the crystals (T%=96.2) obtained in Example 5, and after sludging at 10° C. for 1 hour, the solution was then filtered. The amount of the obtained crystals was 43.4 g (dry weight) and T% was 98.5.

COMPARATIVE EXAMPLE 1

By the use of an aqueous L-phenylalanine solution containing 48.0 g of L-phenylalanine and 4.8 g of cinnamic acid and having a pH of 4.0 before extraction with toluene in the procedure of Example 1, the following operation was conducted. The solution was concentrated at 70° C. under reduced pressure until the concentration of L-phenylalanine was 10% by weight. There the solution was then filtered, while the concentration temperature was maintained, to separate the crystals of L-phenylalanine which precipitated therefrom. The thus obtained crystals were washed with warm water at 70° C. in about the same amount as the crystals. The filtrate and the wash liquid were subjected to the similar operations of concentration and filtration again, and this cycle was repeated 7 times in all. The amount of the obtained crystals was 42.3 g (dry weight) in all, and that of cinnamic acid contained therein was 0.1%.

COMPARATIVE EXAMPLE 2

800 g of an original solution to be concentrated containing 48.0 g of L-phenylalanine and 4.8 g of cinnamic acid before extraction with toluene in the procedure of Example 1, were concentrated at 70° C. under reduced pressure until the concentration of L-phenylalanine was 20% by weight. Afterward, crystallization was carried out at 10° C. for 1 hour, followed by filtration. The weight of the thus obtained crystals was 41.2 g (dry weight) the of cinnamic acid content thereof was 0.2%.

COMPARATIVE EXAMPLE 3

800 g of an original solution to be concentrated, containing 48.0 g of L-phenylalanine and 4.8 g of cinnamic acid before extraction with toluene in the procedure of Example 1, were concentrated at 70° C. under reduced pressure until the concentration of L-phenylalanine was 20% by weight. Afterward, 240 g of a 80% aqueous isopropyl alcohol solution were added to the concentrated solution, followed by cooling. Next, crystallization was carried out at 10° C for 1 hour, followed by filtration. The weight of the thus obtained crystals was 40.8 g (dry weight) and the cinnamic acid content thereof was 0.1%.

TABLE 1

|  | Example 2 | Example 3 | Example 4 |
|---|---|---|---|
| Original Solution to be Concentrated | | | |
| L-phenylalanine (g) | 47.6 | 48.0 | 47.9 |
| Cinnamic Acid (g) | 1.5 | 1.6 | 1.5 |
| Solid Phase | | | |
| L-phenylalanine (g) | 45.7 | 45.6 | 45.6 |
| Cinnamic Acid (g) | not detected | not detected | not detected |

We claim:
1. A method for purifying L-phenylalanine which comprises the steps of:
   (a) subjecting an aqueous solution containing mainly cinnamic acid and L-phenylalanine to toluene extraction to extract cinnamic acid therefrom followed by separating the extracting toluene solution from the extracting aqueous solution;
   (b) concentrating as an aqueous phase concurrently with the separated extracted aqueous solution until a solid phase comprising L-phenylalanine forms therein;
   (c) collecting a solid phase comprising the solid phase comprising crystals of L-phenylalanine separated in said step (b).
2. The method according to claim 1 wherein said extraction of cinnamic acid is carried out at a pH of less than 5.
3. The method according to claim 1, wherein Step (c) is conducted in a decanter type centrifugal settler.
4. The method according to claim 1 wherein a lower alcohol is added to said separated solid phase.
5. The method according to claim 4 wherein said lower alcohol is selected from the group consisting of isopropyl alcohol, n-propyl alcohol, methyl alcohol and ethyl alcohol.
6. The method according to claim 4 wherein the amount of said lower alcohol which is added is from 50 to 150% by weight based on the weight of L-phenylalanine.
7. A method for preparing and isolating L-phenylalanine in pure form which comprises the steps of:
   (i) reacting cinnamic acid with an ammonia source in the presence of phenylalanine ammonia lyase to obtain a reaction solution;
   (ii) clarifying said reaction solution to obtain a clarified liquid;
   (iii) removing said ammonia source from said clarified liquid;
   (iv) extracting said clarified liquid obtained in step (iii) with toluene and then separating the resulting toluene phase from the thus-extracted aqueous phase;
   (v) concentrating the extracted aqueous phase obtained in step (iv) until a solid phase forms therein while concurrently subjecting said aqueous phase to a solid/liquid separation and recycling the separated liquid phase back to said aqueous phase; and
   (vi) recovering the solid phase consisting essentially of pure L-phenylalanine crystals obtained in said step (v).
8. The method according to claim 7 wherein said extraction of cinnamic acid is carried out at a pH of less than 5.
9. The method according to claim 7 wherein step (v) is conducted in a decanter type centrifugal settler.
10. The method according to claim 7 wherein said aqueous ammonia-free solution obtained in step (iii) is subjected to an active carbon treatment prior to step (iv).
11. The method according to claim 7 wherein a lower alcohol is added to said solid phase obtained by said concentration to achieve sludging.
12. The method according to claim 11 wherein said lower alcohol is selected from the group consisting of isopropyl alcohol, n-propyl alcohol, methyl alcohol and ethyl alcohol.
13. The method according to claim 11 wherein the amount of said lower alcohol which is added is from 50 to 150% by weight based on the weight of L-phenylalanine.
14. A method for isolating L-phenylalanine in pure form which comprises the steps of (a) subjecting an aqueous solution containing mainly cinnamic acid and L-phenylalanine to toluene extraction to extract cinnamic acid therefrom followed by separating the extracting toluene solution from the extracted aqueous solution; (b) concentrating as an aqueous liquid phase the separated extracted aqueous solution until a solid phase comprising crystals of L-phenylalanine forms therein; and (c), concurrently with step (b), separating by solid/liquid separation the solid phase comprising crystals of L-phenylalanine from the aqueous liquid phase.
15. The method according to claim 14 wherein the starting solution employed in step (a) contains 4% to 6% L-phenylalanine and between 0.01% and 0.6% by weight cinnamic acid.
16. The method according to claim 14 wherein step (a) is conducted at a pH no greater than 4.5 and at a temperature of 60°–80°.
17. The method according to claim 14 wherein the temperature at which step (b) is conducted is between 50° and 70° C.
18. The method according to claim 14 wherein the concentration and solid/liquid separation of steps (b) and (c) are both conducted intermittently a plurality of times.
19. The method according to claim 14 wherein the starting solution employed in step (a) contains 4% to 6% L-phenylalanine and between 0.01% and 0.6% by weight cinnamic acid; wherein step (a) is conducted at a pH no greater than 4.5 and at a temperature of 60°–80° with less than 50 parts of toluene by weight of the aqueous solution; wherein the temperature at which step (b) is conducted is at up to 70° C.; and wherein the concentra- tion and solid/liquid separation of steps (b) and (c) are both conducted intermittently a plurality of times.

20. The method according to claim 14 wherein the starting solution for step (a) is the solution obtained by removing the suspended solids and ammonia source from the reaction solution obtained by reacting cinnamic acid with an ammonia source in the presence of phenylalanine ammonia lyase.

* * * * *